United States Patent
Gottschalk et al.

(10) Patent No.: US 11,230,484 B2
(45) Date of Patent: Jan. 25, 2022

(54) METHODS AND SYSTEMS FOR CALCITE REMOVAL USING POLYSUCCINIMIDE

(71) Applicant: CHEMTREAT, INC., Glen Allen, VA (US)

(72) Inventors: Kevin Michael Gottschalk, Richmond, VA (US); Phil Godsave, Cranbrook (CA); Raymond M Post, Langhorne, PA (US); Robert W. Bedinger, Mechanicsville, VA (US)

(73) Assignee: CHEMTREAT, INC., Glen Allen, VA (US)

( * ) Notice: Subject to any disclaimer, the term of this patent is extended or adjusted under 35 U.S.C. 154(b) by 0 days.

(21) Appl. No.: 16/568,794

(22) Filed: Sep. 12, 2019

(65) Prior Publication Data
US 2020/0079673 A1  Mar. 12, 2020

Related U.S. Application Data

(60) Provisional application No. 62/730,442, filed on Sep. 12, 2018.

(51) Int. Cl.
| | | |
|---|---|---|
| *C02F 5/12* | (2006.01) | |
| *G01N 21/64* | (2006.01) | |
| *G01N 33/18* | (2006.01) | |
| *C02F 101/10* | (2006.01) | |
| *C02F 103/10* | (2006.01) | |

(52) U.S. Cl.
CPC ............ *C02F 5/12* (2013.01); *G01N 21/6428* (2013.01); *G01N 33/1886* (2013.01); *C02F 2101/10* (2013.01); *C02F 2103/10* (2013.01); *C02F 2209/001* (2013.01); *C02F 2209/40* (2013.01); *C02F 2305/14* (2013.01)

(58) Field of Classification Search
CPC ........ C02F 1/008; C02F 1/66; C02F 2101/10; C02F 2103/10; C02F 2209/001; C02F 2209/005; C02F 2209/02; C02F 2209/06; C02F 2209/40; C02F 2301/043; C02F 2305/14; C02F 5/12; G01N 21/6428; G01N 33/1886
See application file for complete search history.

(56) References Cited

U.S. PATENT DOCUMENTS

| | | | |
|---|---|---|---|
| 2014/0083949 A1* | 3/2014 | Takahashi | ................. F03G 7/04 210/696 |
| 2015/0122628 A1* | 5/2015 | Spaeth | .................... C10B 43/08 201/2 |

FOREIGN PATENT DOCUMENTS

DE           2009092353       *   7/2009

OTHER PUBLICATIONS

English language translation of "Wasserwirtschaft 94(4):32-37, Apr. 2004", 20 Pages, Translated: Dec. 2020. (Year: 2020).*

(Continued)

*Primary Examiner* — Pranav N Patel
(74) *Attorney, Agent, or Firm* — Oliff PLC

(57) ABSTRACT

Methods and systems are provided for removing calcite deposits by contacting polysuccinimide with water to dissolve the polysuccinimide and supplying the dissolved polysuccinimide to surfaces fouled with the calcite deposits. The pH of the water that dissolves the polysuccinimide can be adjusted based on the amount of calcium in the water. Adjusting the pH will affect the dissolution rate of the polysuccinimide in water and the rate of removal of the calcite deposits.

10 Claims, 1 Drawing Sheet

(56) References Cited

OTHER PUBLICATIONS

English language machine translation of WO2009092353, 7 pages. No Date.*

Klein, T. et al., "Hydrolysis of Polysuccinimide and Its Effect Against Sintering in Tunnels", Wasserwirtschaft, Apr. 2004, pp. 32-36.

Moritz, R. "Reduction of Tunnel Maintenance Costs By Environmentally Friendly Water Hardness Stabilization", World Tunnel Congress 2009, May 26, 2009.

Baypure DSP Tabs 100 Product Information, Precursor to biodegradable anti-scaling & dispersing agents. Jul. 2004.

Mosig, J. et al. "Kinetic and Thermal Characterization of the Hydrolysis of Polysuccinimide", Ind. Eng. Chem. Res., vol. 36, 1997, p. 2163-2170.

* cited by examiner

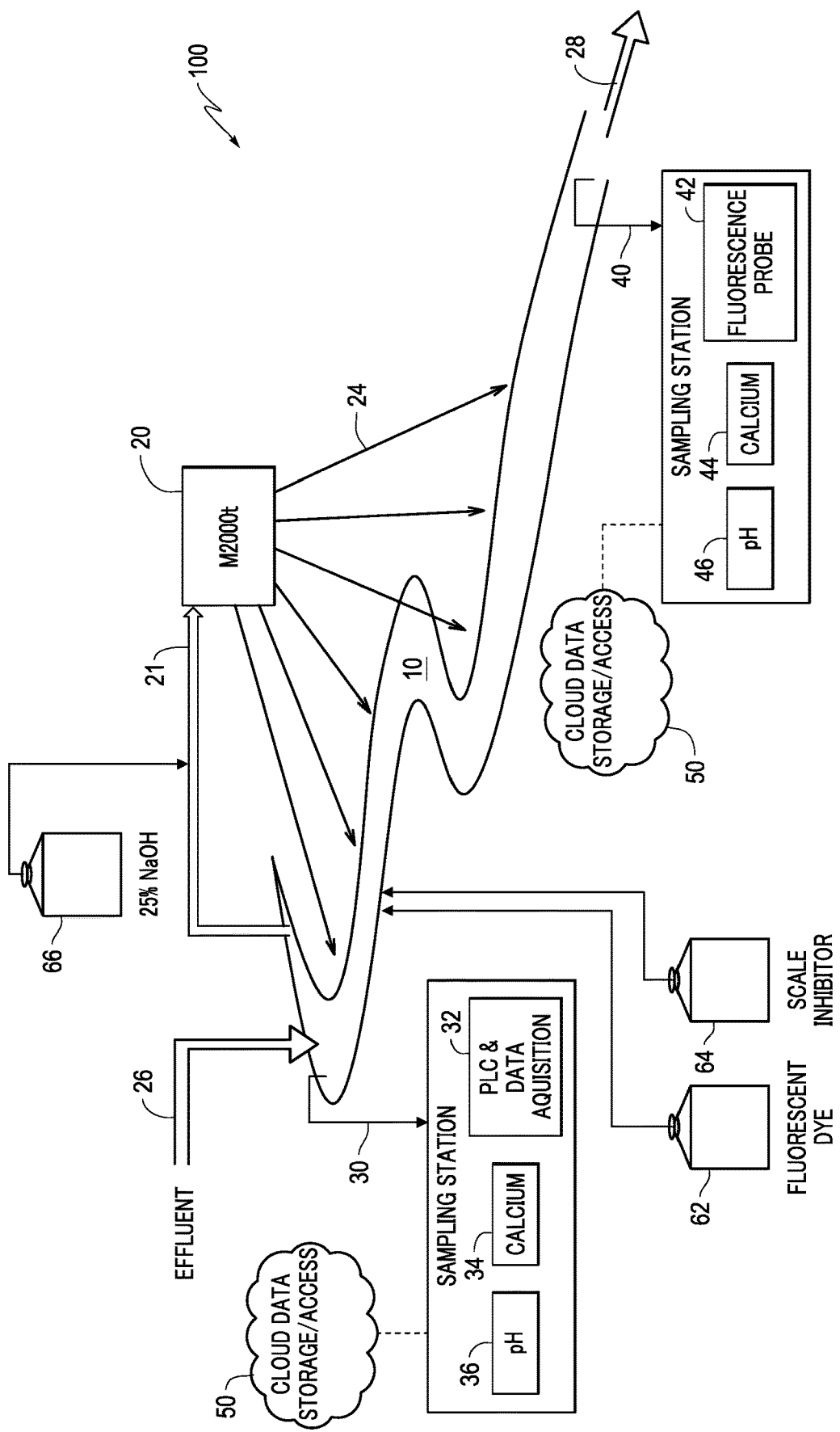

METHODS AND SYSTEMS FOR CALCITE REMOVAL USING POLYSUCCINIMIDE

CROSS-REFERENCE TO RELATED APPLICATION

This application claims the benefit of the earlier filing date of U.S. Provisional Application No. 62/730,442, which was filed on Sep. 12, 2018. The entirety of this provisional application is incorporated by reference herein.

TECHNICAL FIELD

This disclosure relates generally to the removal of calcite deposits in water bearing systems by using polysuccinimide, and more particularly to a novel feed and control monitoring system for facilitating remediation and clean-up of existing calcite deposits in stream beds.

BACKGROUND

Mining companies in North America and throughout the world often discharge highly scale forming waters so over time the receiving stream becomes heavily fouled with calcium carbonate (calcite) and calcium sulfate (gypsum) and other inorganic minerals that will precipitate as the effluent water carbon dioxide is stripped out, which leaves major (hundreds of tons) of deposits in the mine or processing plant effluent.

Various solutions have been trialed including manual cleaning of the deposits, addition of scale control reagents which might in theory remove a very small fraction of the deposit, mineral acids such as hydrochloric acid. However, current methods of applying scale control reagents are not effective at clean-up, and the use of huge volumes of mineral acids to remove the existing calcite deposits would be harmful to the environment.

SUMMARY

In some aspects, the feed and control monitoring system described herein can enable an operator to adjust the rate of clean up by using the novel properties of solid forms of polysuccinimide, and remove the deposits over time as a function of parameter(s) such as the stream pH, calcium levels, and stream flow rate. These and other variables monitored and controlled by the sophisticated water chemistry monitoring station at the stream inlet and stream outlet to the receiving waters.

In one aspect, this disclosure provides a method for treating a water system to remove calcite deposits. The method includes measuring an amount of dissolved calcium in the water system, contacting polysuccinimide with water in the water system to dissolve the polysuccinimide and to provide treatment water containing the dissolved polysuccinimide and/or hydrolysis products of the dissolved polysuccinimide, supplying the treatment water to surfaces of the water system that are fouled with calcite deposits, and adding an alkali reagent to the water to increase the pH of the water and to increase a rate of dissolution of the polysuccinimide in the water. In general, an amount of the alkali reagent that is added to the water can be based on the measured amount of dissolved calcium in the water system.

In another aspect, this disclosure provides a system for treating surfaces fouled with calcite. The system includes a remediation water stream that includes a stream bed with surfaces fouled with calcite, a split stream that has an influent supplied by the water stream and an effluent that is fed back to the water stream, a feed source of solid polysuccinimide that is contacted by water from the split stream to dissolve the polysuccinimide so that dissolved polysuccinimide is supplied from the split stream to the remediation water stream, a calcium probe that is configured to measure an amount of dissolved calcium in the remediation water stream and/or split stream, a pH probe that is configured to measure the pH of the remediation water stream and/or split stream, and an alkali source that is configured to supply an alkali reagent to the remediation water stream and/or split stream. The system can be configured so that an amount of the alkali agent that is supplied is based on at least the measured amount of dissolved calcium.

BRIEF DESCRIPTION OF THE DRAWINGS

The drawing is a schematic diagram illustrating a calcite remediation system for a mine effluent stream.

DETAILED DESCRIPTION OF EMBODIMENTS

In some aspects, the systems and methods described herein integrate the use of a well-known and environmentally friendly chemical polysuccinimide with a sophisticated water sensor platform to constantly monitor the flow in water bearing systems (e.g., mine effluent streams), the water pH, the water calcium hardness level and/or other variables that allow the system operator to adjust the addition rate of dissolved polysuccinimide to the stream to much more rapidly and safely clean up the stream and return it to its natural condition. Thus, the rate of calcite (calcium carbonate) removal from heavily fouled streams can be optimized for removal by adding polysuccinimide, e.g., by constantly or periodically adjusting key water chemistry variables and using on-line analyzers for pH, calcium hardness, fluorescent dyes, and/or other water parameters. The methods and systems described herein thus provide a unique and effective way of monitoring and controlling the addition of polysuccinimide to a water system in a manner that is environmentally friendly to the receiving stream (including, e.g., comporting with established best practices in Europe). In some cases, the methods and systems described herein can be useful for remediating calcite deposits that are up to 20 inches thick or more, including from 0.5 to 15 inches, 2 to 12 inches, or from 4 to 6 inches thick.

Polysuccinimide can be added to the water bearing system to remove existing calcite deposits and perhaps prevent scale from forming. The polysuccinimide can be added in solid form, e.g., as tablets or powder or granules, and dissolved so that effective dissolved amounts are present in the system to remove existing calcite deposits. The solid polysuccinimide can be at least 50 wt. % polysuccinimide, at least 80% polysuccinimide, or at least 90% polysuccinimide, and may also include other components such as binders. The polysuccinimide may have a molecular weight that is in a range of from 500-15,000 g/mol, 1,000 to 10,000 g/mol, or 2,000 to 5,000 g/mol.

In one aspect, this disclosure enables the system operator to control the dissolved amount of polysuccinimide in the stream by controlling the pH of the polysuccinimide feed stream (e.g., with the addition of sodium hydroxide or other alkali reagent) to maximize the rate of calcite removal based on known pH curves (published by LANXESS Corporation and other sources). For example, at pH 8, slightly higher than normal stream pH, the rate of calcite removal is approximately double the calcite removal at pH 7, and at pH 9, typically the upper safe limit of this method (per most effluent discharge permit limits) the rate of calcite removal is doubled again compared to a stream pH of 8. In general, there is a 1st order kinetic relationship between water pH and dissolution rate of the polysuccinimide. The pH of the polysuccinimide feed stream thus can be controlled to be within a range of 7-10, 8-9.5, or 8.5-9.5 depending on the desired amount of dissolved polysuccinimide. The pH of the water can be measured by an on-line pH meter, for example, at a location that is proximate to or upstream of the location where the solid polysuccinimide is dissolved in water.

Another variable that can be manipulated to control the dissolved amount of polysuccinimide in the stream is the water flow rate that contacts the polysuccinimide since more polysuccinimide will dissolve at higher flow rates. The size of the solid polysuccinimide particles will also affect the dissolution rate. For example, tablets will dissolve more slowly than a granular form, and smaller particles will generally dissolve more quickly than larger particles. Accordingly, in considering the dissolution rate of the solid polysuccinimide, the water flow rate and particle size can be considered.

As described in greater detail below, the desired dissolved amount of polysuccinimide that is added can be determined based on the amount of dissolved calcium that is being added to the remediation stream, the amount of dissolved calcium exiting the remediation stream, turbidity differences across the stream, the amount of existing calcite deposits, and/or the desired rate of remediation.

In some embodiments, the solid polysuccinimide can be added directly to the stream that is being remediated. In other embodiments the solid polyscuccinimide can be added in slip streams that are diverted from the remediation stream, e.g., by pumps, or can be added in side streams that are supplied to the remediation stream. In all cases, the solid polysuccinimide can be contacted with water to dissolve it and carry the dissolved polysuccinimide and/or hydrolysis products thereof downstream to a remediation area containing calcite deposits. In embodiments, the solid polysuccinimide can be added to a flow through feeder, such as brominator, that is provided in the stream, and the solid polysuccinimide can be resupplied to the feeder periodically or as needed.

The solid polysuccinimide can be supplied to the water at locations and time intervals that are sufficient to react with and consume and dissolve the existing calcite deposits. In many cases, effective treatments can be achieved by supplying at intervals that are in a range of 1 to 20 times per year, 2 to 20 times per year, 3 to 10 times per year, or 4 to 5 times per year. In this regard, the polysuccinimide will likely applied each quarter or twice per year or at whatever rate is necessary to continue the clean up as required by the state or local regulatory authorities. Suitable usage amounts of polysuccinimide may be within a range from 0.01 to 50 kg/m$^3$ per day, 0.05 to 15 kg/m$^3$ per day, or 0.1 to 5 kg/m$^3$ per day based on the volume of water in the remediation stream.

The polysuccinimide chemistry is well understood by those skilled in the art of organic chemistry and is produced commercially in large quantities (many thousand tons/yr) because it is the production intermediate for biodegradable dispersants and chelants such as polyaspartic acid and immunodisuccinate, and these two ((break down products" are environmentally friendly and biodegradable under the European OECD 301B standard for biodegradability (more than 60% biodegradable within 30 days per standard OECD301B open headspace methods and similar).

In one aspect, to determine the dissolved calcium in the system, calcium analyzers/probes can be used. The calcium analyzer can be present at the stream influent (where the calcium-containing process stream is added) and/or at the stream effluent. The calcium analyzers can measure the amount of dissolved calcium in the influent and effluent so that the amount of calcium that is removed from or added to the system can be roughly calculated by mass balance. This calculation may be improved by turbidity sensors that measure turbidity of the water at the influent and/or effluent, which may be correlated to calcium-based particles that are present in the water but not dissolved. In this regard, it is possible that the polysuccinimide removes some of the calcite deposit as chunks or particles where the calcium is not dissolved. The monitoring station can take the inlet and outlet calcium and turbidity levels, calculate the delta change and multiply these values by the flow rate in the stream to determine very accurately the rate of clean up or deposition (in the case of scale forming conditions in the water and insufficient scale inhibition inhibitors present in the water system). In contrast, using conventional techniques, the operators can only make educated guesses if the stream cleanup is occurring.

The calcium concentration at the influent and the flow rate are an indication of the amount of calcium that is being put into the stream, and that information can be used to control the dissolution rate of the polysuccinimide. For example, if there are spikes in the amount of calcium entering the stream, the pH of the polysuccinimide pH water can be increased to around 8.5 or 9 to increase the rate of dissolution and supply more dissolved polysuccinimide to the remediation stream to, in turn, increase the rate of calcite removal.

The water temperature is also a variable that can be considered in controlling the dissolution rate of polysuccinimide. The temperature of many process streams, particularly outdoor mine remediation streams, will vary seasonally, and temperature affects the rate at which the calcite builds up. In general, cold water is less scale forming, and there are also lower calcium levels with more winter and spring snow melt run off. Thus, in some aspects, the methods and systems described herein can measure the water temperature (e.g., with a thermometer or thermocouple) and use the temperature information in determining the water pH to control the dissolution rate of polysuccinimide.

In another aspect, the methods and systems of this disclosure can employ a fluorescent dye (e.g., a combination of fluorescein and PTSA, as described in U.S. Pat. No. 10,024,751, the entirety of which is incorporated by reference herein) and a probe monitoring device. This can allow for very accurate stream flow measurement by periodically injecting the dye upstream and then measuring (to as low as 10 ppb) the dye levels in fluorimeter (e.g., twin probe fluorimeter) to calculate the stream flow to very precise accuracy.

The breakdown products of polysuccinimide include predominately polyaspartate, which has a specific fluorescence profile which can also be analyzed in real time by the monitoring platform, with different fluorescence properties than the two dye (fluorescein and PTSA) and other dye-based reagents. The measured amount of polyaspartate may be of interest because polyaspartate is an active scale inhibitor, and further the amount of polyaspartate may be correlated with the amount of dissolved polysuccinimide that has been added to the system, and thus is useful information that can also be used to control the rate of amount of dissolved polysuccinimide in the water, e.g., by adjusting pH. The chemistry of polyaspartate to regulate calcium carbonate growth and crystal deposit is well understood by scientists, and is the same chemistry as utilized in nature by oysters to regulate the calcium carbonate growth of their oyster shells. That polyaspartate is produced by the synthesis via amino acid method, whereas polysuccinimide can be synthesized by method using maleic anhydride and highly specialized large chemical production methods, and this chemistry is available in sufficient quantities for the desired clean up results at the sites needing calcite removal at cost effective reagent costs.

The drawing is a schematic diagram illustrating how a monitoring and feed control system 100 can work to remediate a stream bed that receives a mine effluent stream 26. In this case, a polysuccinimide source 20 (e.g., ChemTreat M2000t tablets) can be dissolved in water from a split stream 21 that is pumped from the remediation stream 10. The dissolved polysuccinimide is then fed to the stream 10 at dosage locations 24. It is also possible that the polysuccinimide could be dissolved directly in the remediation stream 10, but the use of a split stream is considered more environmentally friendly and it also may be easier to control the pH of the split stream.

A first sampling station 30 is provided near the mine effluent (remediation stream influent), and includes a programmable logic controller (PLC) and data acquisition unit 32, a calcium analyzer 34, and pH meter 36. The pH values and calcium concentration values can be collected and determined by the PLC and data acquisition unit 32 and transmitted to the cloud 50 for storage or further processing. A second sampling station 40 is provided near the stream effluent 28 and may include a calcium analyzer 44, a pH meter 46, and a fluorescent probe 42. The pH values, calcium concentration values, and fluorescence absorption/emission values can be gathered and transmitted to the cloud 50 for storage or further processing. The set up and location of the sampling stations in the diagram is for illustration only. Various ones of these sensors or combinations of these sensors can be included at each sampling station and the sensors can be included at different locations on the remediation stream, a slip stream, or a side stream.

The system 100 includes a fluorescent dye tank 62 that includes a fluorescent dye or combination of dyes that can be pumped into the remediation stream 10 for determining the stream flow rate and/or polyaspartate concentrations, as described above. The system 100 can also include a scale inhibitor tank 64 that includes one or more scale inhibitors that can be pumped into the remediation stream for preventing further scale formation. The system 100 can also include an alkali tank 66 that includes a pH adjusting agent such as sodium hydroxide that can be pumped to various positions in system 100 to control the pH of the water. As shown in the drawing, it may be desirable to control the pH of the water proximate to the polysuccinimide source 20 such as the split stream 21, and thus the alkali tank 66 can be configured to pump the pH adjusting agent to the split stream 21 at a location that is upstream of the polysuccinimide source 20. The alkali tank 66 and/or the pump can be automatically and continuously controlled by controller, such as a CPU, that adjusts the amount of pH adjusting agent that is added to the water based on one or more feedback loop mechanisms (e.g., PID controller), for example, by using the readings from one or more of the calcium probe, pH probe, temperature sensor, fluorescent probe, and turbidity probe (not shown). In general, if more total calcium is being added to the stream, the pH of the water dissolving the polysuccinimide should be increased, and if relatively lower amounts of total calcium are being added to the stream, lower or normal pH levels may be acceptable.

All the data collected by the sensors can be fed by a network interface such as a cellular modem to a computer network, e.g., the cloud, where it can be stored in a memory, processed by a controller to generate control signals, processed by a controller to display information, and easily accessed in real time by the system operator to be able to make any adjustments in the system parameters.

While the invention has been described in conjunction with the specific exemplary embodiments thereof, it is evident that many alternatives, modifications, and variations will be apparent to those skilled in the art. Accordingly, exemplary embodiments of the invention as set forth herein are intended to be illustrative, not limiting. There are changes that may be made without departing from the spirit and scope of the invention.

What is claimed is:

1. A system for treating surfaces fouled with calcite, the system comprising:
    a remediation water stream that includes a stream bed with the surfaces fouled with calcite;
    a split stream that has an influent supplied by the remediation water stream and an effluent that is fed back to the remediation water stream at a plurality of locations;
    a feed source of solid polysuccinimide that is contacted by water from the split stream to dissolve the polysuccinimide so that dissolved polysuccinimide is supplied from the split stream to the remediation water stream at the plurality of the locations;
    a calcium probe that is configured to measure an amount of dissolved calcium in the remediation water stream and/or split stream;
    a pH probe that is configured to measure the pH of the remediation water stream and/or split stream; and
    an alkali source that is configured to supply an alkali reagent to the split stream,
    wherein the system is configured so that an amount of the alkali agent that is supplied is based on at least the measured amount of dissolved calcium.

2. The system according to claim 1, further including a controller that is configured to control an amount of the alkali agent that is supplied based on the measured amount of dissolved calcium.

3. The system according to claim 2, wherein the controller is also configured to control an amount of the alkali agent that is supplied based on the measured pH.

4. The system according to claim 2, wherein the controller is configured to increase an amount of the alkali agent that is supplied if the measured amount of dissolved calcium increases.

5. The system according to claim 1, further comprising a fluorescent dye source that is configured to supply at least one fluorescent dye to the water stream, and a fluorimeter that is configured to measure fluorescence of the at least one fluorescent dye.

6. The system according to claim 5, further including a controller that is configured to determine a flow rate of the remediation water stream based on the measured fluorescence.

7. The system according to claim 6, wherein the controller is also configured to control an amount of the alkali agent that is supplied based on the flow rate of the remediation water stream.

8. The system according to claim 1, wherein the split stream is maintained at pH values within the range of 7 to 10.

9. The system according to claim 1, wherein the split stream is maintained at pH values within the range of 8 to 9.5.

10. The system according to claim 1, wherein the split stream is maintained at pH values within the range of 8.5 to 9.5.

\* \* \* \* \*